United States Patent [19]

Moineau et al.

[11] Patent Number: 5,994,118
[45] Date of Patent: Nov. 30, 1999

[54] DNA ENCODING PHAGE RESISTANCE PROTEIN

[75] Inventors: Sylvain Moineau, Charlesbourg; Eric Emond, Sillery, both of Canada; Shirley A. Walker, Raleigh, N.C.; Ebenezer R. Vedamuthu; Jeffrey K. Kondo, both of Rochester, Minn.

[73] Assignee: Quest International B.V., Naarden, Netherlands

[21] Appl. No.: 08/980,329

[22] Filed: Nov. 28, 1997

[51] Int. Cl.$^6$ ............................. C12N 1/20; C12N 15/00; C07H 17/00; C07K 14/00
[52] U.S. Cl. ................................ 435/252.9; 435/320.1; 435/69.1; 536/23.7; 530/350
[58] Field of Search ............................ 530/350; 536/23.7; 435/252.9, 320.1, 69.1

[56] References Cited

PUBLICATIONS

Jarvis, et al, Invervirology 32:2–9 (1991).
Moineau, et al, J. Dairy Sci. 79:2104–2111 (1996).
Garvey et al., Int. Dairy J. 5:905–947 (1995).
Sing, W.S. et al, J. Dairy Sci. 73:2239–2251 (1990).
Hill et al., Appl. Environ, Microbiol 56:3547–3551 (1991).
Durmaz et al., J. Bacteriol. 174:7463–7469 (1992).
McLandsborough et al., Appl. Environ. Microbiol. 61:2023:2026 (1995).
Anaba et al., J. Bacteriol 177:3818–3823 (1995).
Garvey et al., Appl. Environ. Microbiol. 61:4321–4328 (1995).
O'Connor et al., Appl. Environ Microbiol. 63:3075–3082 (1996).
Prévots et al., FEMS Microbiol. Lett 142:295–299 (1996).
Deng et al., FEMS Microbiol. Lett 146:149–154 (1997).
Emond et al., Appl. Environ. Mircobiol 63:1274–1283 (1997).
alatossava et al., Appl. Environ. Microbiol. 57:1346–1353 (1991).
Moineau et al., Appl. Environ. Microbiol. 56:197–202 (1993).
Jarvis, A.W., APpl Environ Microbiol. 36:785–789 (1978).
Sanders, M.E., et al., Appl. Environ Microbiol. 40:500–506 (1980).
Behnke, D., et al., Virology 85:118–128 (1978).
O'Sullivan, D.J., et al., Appl. Environ. Microbiol. 59:2730–2733 (1993).
Holo and Nes, Appl. Environ. Microbiol. 55:3119–3123 (1989).
Devereux et al., Nucleic Acids Res. 12:387–395 (1994).
Hobohm and Sanders, J. Mol Biol. 251:390–399 (1995).
Ludwig, et al., J. Gen. Microbiol. 131:543–551 (1985).
Freier, S.M. et al., Proc Natl. Acad. Sci. USA 83:9373–9377 (1986).
Terzaghi and Sandine, Appl. Environ Microbiol. 29:807–813 (1976).

*Primary Examiner*—Karen Cochrane Carlson
*Attorney, Agent, or Firm*—Ian C. McLeod

[57] ABSTRACT

A novel protein (Abi900, 183 amino acids) and its gene were isolated from a 11-kb natural plasmid (pSRQ900) of *Lactococcus lactis*. When pSRQ900 is introduced into dairy starter cultures, the Abi900 protein confers strong resistance to bacteriophage infection.

21 Claims, 5 Drawing Sheets

```
GATATCGGAC TCGCTATATA CAAGCATGAT TCTTTACCTA TCTATGTTCA AGGGGGAAGT    60
ATCTTATATG TTAAAACATC AAAATGTGAA AATTAGACG GTTTATTTTT AAAATATTCT   120
TTGCTTCCC CTAAAGTAAA AAATATATT AGAAATGCTT CAACAGGAAC GAGCTTAAAA    180
CATTTGTTT TGAAACCAGC TAATGCTCTT CCAATGTCAT ATCCAGATTT GATGAGCAA    240
GAAAAAATTG GTTCATTATT AATGCAAATG GATCGCCACTA TCACTCTTCA TCAACGTAAG  300
TTAGATTTGT TGAAAGAACA GAAAAAAGGC TTTTTACAAA AGATGTTTGT TTAGGGTCTA   360
TAATTAGATA ATAGCCCCTT AGAAATACAA TAAAAACAGC CCCTATATC TAACACTTAG   420
ATAATGGGGG CTGTTTTCTT ATTTTTTATC AATATAACCC GTCCAAGGAA TATACAAAAA  480
GAACCGAAGA AATGGAACGC TCTTCGGATT TTCGTATCT ACTGAGATTA AGTGTCTTAAT  540
GGGAATATTA GCTTAAGAAC AAGAAGGATT ATAAACCTTG TATTTGATTT TTAAACTTTG  600
                                          -35
CAACAGAACC GTTTTTATT ACCAAAAAAT ATTTCTTGCA TTTTTATATA TGGTATGATA    660
     -10
TTATAATTGT AAGGAATATC CAAGCCATAG TTGGAATTGA TAAAATTGGA GTATCCAAGC   720
                                                       RBS
CATAGTTGGA ATTGATAAAA TTGGAGTATC CAAGCCATAG TTGGAATTGA TAAAAGCTAC   780

TCT ATG AGT AGC ACT TTT TTT TAT AAG GAG ATT TTA CGA ATG TTA AGA TTC TTT ACT GTA   840
    Met Ser Ser Thr Phe Phe Tyr Lys Glu Ile Leu Arg Met Leu Arg Phe Phe Thr Val
             5                           10                           15

ACT GAT GAA TAT ATA GCT TAT TTA CGT AAG TTT GAA AGT AAA GTT CAT TAT CAA TAT GAA   900
Thr Asp Glu Tyr Ile Ala Tyr Leu Arg Lys Phe Glu Ser Lys Val His Tyr Gln Tyr Glu
         20                           25                           30                           35

AAT AAT GCC AGC ACT TAT GTA GGG GTT GTT TTG AAA AAG AAT GAT TTC AAT TAC TTT ATA   960
Asn Asn Ala Ser Thr Tyr Val Gly Val Val Leu Lys Lys Asn Asp Phe Asn Tyr Phe Ile
         40                           45                           50                           55

CCT TTG TCA AGC TAC AAA AAG GGG AAC CCC GAG AAA GAC AAA GCA ATG AAA AAA AGA AGT  1020
Pro Leu Ser Ser Tyr Lys Lys Gly Asn Pro Glu Lys Asp Lys Ala Met Lys Lys Arg Ser
         60                           65                           70                           75
```

FIG. 3A

```
CGA ATA GTA ACT AGA CTT TTT GAA ATT GGC AAT ATA AAT CCT CTT GGA TAT TTA TTA   1080
Arg Ile Val Thr Arg Leu Phe Glu Ile Gly Asn Ile Asn Pro Leu Gly Tyr Leu Leu
 80                      85                      90                      95

CAT CAT AAT ATG ATT CCA GTT CCT GAC AGC GAA TTA ATA CCC CTA CCT TTA GAT CTT AAG   1140
His His Asn Met Ile Pro Val Pro Asp Ser Glu Leu Ile Pro Leu Pro Leu Asp Leu Lys
100                     105                     110                     115

AAA CCT AAA CAT AAA ATG ATG CAA AAA CAA CTA ATT TAT ATG AAA AGT ATC AGC GAA AAA   1200
Lys Pro Lys His Lys Met Met Gln Lys Gln Leu Ile Tyr Met Lys Ser Ile Ser Glu Lys
120                     125                     130                     135

ATT GAA AAT AAA TCT GAA GTG GTA TAT AGA AAA GCT GCT CAT GAA AAA GAT GGA TAT TAC   1260
Ile Glu Asn Lys Ser Glu Val Val Tyr Arg Lys Ala Ala His Glu Lys Asp Gly Tyr Tyr
140                     145                     150                     155

TTA AAA TTT TCC TGT GAT TTT AAA CTA CTA GAA GCT AAA GCA ACA TTA TAT TCT AAG AAA   1320
Leu Lys Phe Ser Cys Asp Phe Lys Leu Leu Glu Ala Lys Ala Thr Leu Tyr Ser Lys Lys
160                     165                     170                     175

TCT ACA TTT CAA TAA TGG AC ATCTCTTTAG CAAGAACTAA GAGATTAAAA ACAAAAGTAA   1380
Ser Thr Phe Gln
180

AAAAACATAC TCTGACGAAT CGAATTATAA ATCAGAATAT GTTTTTTTT GCTTTTTAA    1440
GAGTCTCCAA AATAACATAA ATTTTGAGGA TAAACAAATC ATATTTCTA TAAAAATATA   1500
CCAGTCATTT AGATTAGAAA CACTCTTATT TTTTCATAAA TTTACCATAA ATGGTGATTT   1560
TTTGCCCTTT TCCTTCACTC ATAATATGAG AATCGCTTAA CTGTGAGGTT CACGGACGTT   1620
```

FIG. 3B

```
ATGAGTGTAC GAAAAATCTT AATTTTCTG AAAAAAGAGT TTTTGTGTAC TGCACGTCTA   1680
TCATTATAAT AGTTATCCT CACATTACTC TTCACTATCA ATTTTCATT AATTATACTA   1740
AAATATAATT AATCTTGAAC AAATAATATT AAACACATATA TATACTCATT CTTATTCTG   1800
GCTATAAATAT TTGTTCTTAT TATTTCTACG TTAAAATCAA CATTTAAATA TTTAATAAAA   1860
TAGTTAGGCT TTAATTGATG CTAAAAAAAA TAATACAAAT AAAAAATTAT GGAACTTTCG   1920
AAAATTATAA CTGTGATGGA GATTTTTGGG ATGGAAAAT ACTTAAAAAT AATATTATTT   1980
ATGCCCCAAA TGGTTCTGGA AAAACGAGCA TATCATTAAT TTTTCAGTCT TTAATGAATA   2040
ATAATAATGA TATAATTTTT AAAAAGAAGA ATCTAAATGT AGAAGGAATG CCAGAAATCA   2100
GGCTTCTTTC TGAAAACGAA GTAGGAGCCG AATCTTTGT TAAGTTTGAT AAAAATGGCT   2160
GGAATGGTAA ATTATCCGAT ATAGAAGTTT TCAACTCTTT TTATTCTCT GATCA         2215
```

FIG. 3C 5,994,118

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 2215
      (B) TYPE: Nucleotide
      (C) STRANDEDNESS: Single
      (D) TOPOLOGY: Linear (ii) MOLECULE TYPE:
      (A) DESCRIPTION: Genomic DNA (iii) HYPOTHETICAL: No (iv) ANTI-SENSE: No (v) FRAGMENT TYPE: N/A (vi) ORIGINAL SOURCE:
      (A) ORGANISM: Lactococcus lactis
      (B) STRAIN:
      (C) INDIVIDUAL ISOLATE: W1
      (D) DEVELOPMENTAL STAGE: N/A
      (E) HAPLOTYPE: N/A
      (F) TISSUE TYPE: N/A
      (G) CELL TYPE: bacterium
      (H) CELL LINE: N/A
      (I) ORGANELLE: N/A (vii) IMMEDIATE SOURCE:
      (A) LIBRARY: genomic
      (B) CLONE: SMQ-21

(viii) POSITION IN GENOME: N/A (ix) FEATURE:
      (A) NAME/KEY: phage abortive infection
      (B) LOCATION: N/A
      (C) IDENTIFICATION METHOD: sequencing
      (D) OTHER INFORMATION: DNA encoding phage resistance (x) PUBLICATION INFORMATION: N/A (xi) SEQUENCE DESCRIPTION: SEQ ID NO: 1:

```
GATATCGGAC TCGCTATATA CAAGCATGAT TCTTTACCTA TCTATGTTCA AGGGGGAAGT      60

ATCTTATATG TTAAAACATC AAAATGTGAA AATTTAGACG GTTTATTTTT AAAATATTCT     120

TTTGCTTCCC CTAAAGTAAA AAAATATATT AGAAATGCTT CAACAGGAAC GAGCTTAAAA     180

CATTTTGTTT TGAAACCAGC TAATGCTCTT CCAATGTCAT ATCCAGATTT GATTGAGCAA     240

GAAAAAATTG GTTCATTATT AATGCAAATG GATCGCACTA TCACTCTTCA TCAACGTAAG     300

TTAGATTTGT TGAAAGAACA GAAAAAAGGC TTTTTACAAA AGATGTTTGT TTAGGGTCTA     360

TAATTAGATA ATAGCCCCTT AGAAATACAA TAAAAACAGC CCCTATTATC TAACACTTAG     420

ATAATGGGGG CTGTTTTCTT ATTTTTTATC AATATAACCC GTCCAAGGAA TATACAAAAA     480

GAACCGAAGA AATGGAACGC TCTTCGGATT TTCGGTATCT ACTGAGATTA AGGTCTTAAT     540

GGGAATATTA GCTTAAGAAC AAGAAGGATT ATAAACCTTG TATTTGATTT TTAAACTTTG     600

CAACAGAACC GTTTTTTATT ACCAAAAAAT ATTTCTTGCA TTTTTATATA TGGTATGATA     660

TTATAATTGT AAGGAATATC CAAGCCATAG TTGGAATTGA TAAAATTGGA GTATCCAAGC     720

CATAGTTGGA ATTGATAAAA TTGGAGTATC CAAGCCATAG TTGGAATTGA TAAAAGCTAC     780

TCT ATG AGT AGC TTT TTT TAT AAG GAG ATT TTA CGA ATG ACG TTA AGA     828
```

```
TTC TTT ACT GTA ACT GAT GAA TAT ATA GCT TAT TTA CGT AAG TTT GAA    876

AGT AAA GTT CAT TAT CAA TAT GAA AAT AAT GCC AGC ACT TAT GTA GGG    924

GTT GTT TTG AAA AAG AAT GAT TTC AAT TAC TTT ATA CCT TTG TCA AGC    972

TAC AAA AAG GGG AAC CCC GAG AAA GAC AAA GCA ATG AAA AAA AGA AGT   1020

CGA ATA GTA ACT AGA CTT TTT GAA ATT GGC AAT ATA AAT AAT CCT CTT   1068

GGA TAT TTA TTA CAT CAT AAT ATG ATT CCA GTT CCT GAC AGC GAA TTA   1116

ATA CCC CTA CCT TTA GAT CTT AAG AAA CCT AAA CAT AAA ATG ATG CAA   1164

AAA CAA CTA ATT TAT ATG AAA AGT ATC AGC GAA AAA ATT GAA AAT AAA   1212

TCT GAA GTG GTA TAT AGA AAA GCT GCT CAT GAA AAA GAT GGA TAT TAC   1260

TTA AAA TTT TCC TGT GAT TTT AAA CTA CTA GAA GCT AAA GCA ACA TTA   1308

TAT TCT AAG AAA TCT ACA TTT CAA TAA TGG AC                        1340

ATCTCTTTAG CAAGAACTAA GAGATTAAAA ACAAAAGTAA                       1380

AAAAACATAC TCTGACGAAT CGAATTATAA ATCAGAATAT GTTTTTTTTT GCTTTTTAA  1440

GAGTCTCCAA AATAACATAA ATTTTGAGGA TAAACAAATC ATATTTTCTA TAAAAATATA 1500

CCAGTCATTT AGATTAGAAA CACTCTTATT TTTTCATAAA TTTACCATAA ATGGTGATTT 1560

TTTGCCCTTT TCCTTCACTC ATAATATGAG AATCGCTTAA CTGTGAGGTT CACGGACGTT 1620

ATGAGTGTAC GAAAAATCTT AATTTTTCTG AAAAAAGAGT TTTTGTGTAC TGCACGTCTA 1680

TCATTATAAT AGGTTATCCT CACATTACTC TTCACTATCA ATTTTTCATT AATTATACTA 1740

AAATATAATT AATCTTGAAC AAATAATATT AAAACATATA TATACTCATT CTTATTTCTG 1800

GCTATAATAT TTGTTCTTAT TATTTCTACG TTAAAATCAA CATTTAAATA TTTAATAAAA 1860

TAGTTAGGCT TTAATTGATG CTAAAAAAAA TAATACAAAT AAAAAATTAT GGAACTTTCG 1920

AAAATTATAA CTGTGATGGA GATTTTTGGG ATGGAAAATT ACTAAAAAT AATATTATTT  1980

ATGCCCCAAA TGGTTCTGGA AAAACGAGCA TATCATTAAT TTTTCAGTCT TAATGAATA  2040

ATAATAATGA TATAATTTTT AAAAAGAAGA ATCTAAATGT AGAAGGAATG CCAGAAATCA 2100

GGCTTCTTTC TGAAAACGAA GTAGGAGCCG AATCTTTTGT TAAGTTTGAT AAAAATGGCT 2160

GGAATGGTAA ATTATCCGAT ATAGAAGTTT TCAACTCTTT TTATTTCTCT GATCA       2215

(2) INFORMATION FOR SEQ ID NO:2:

(i) SEQUENCE CHARACTERISTICS:
        (A) LENGTH: 183
        (B) TYPE: Amino Acid
        (C) STRANDEDNESS: Single
        (D) TOPOLOGY: Linear (ii) MOLECULE TYPE:
        (A) DESCRIPTION: Protein (iii) HYPOTHETICAL: No (iv) ANTI-SENSE: No (v) FRAGMENT TYPE: N/A (vi) ORIGINAL SOURCE:
        (A) ORGANISM: Lactococcus lactis
        (B) STRAIN:
        (C) INDIVIDUAL ISOLATE: W1
        (D) DEVELOPMENTAL STAGE: N/A
        (E) HAPLOTYPE: N/A
        (F) TISSUE TYPE: N/A
        (G) CELL TYPE: bacterium
        (H) CELL LINE: N/A
```

```
                    (I) ORGANELLE:  N/A (vii) IMMEDIATE SOURCE:
                    (A) LIBRARY:  genomic
                    (B) CLONE:  SMQ-21

(viii) POSITION IN GENOME:  N/A (ix) FEATURE:
                    (A) NAME/KEY:  phage abortive infection
                    (B) LOCATION:  N/A
                    (C) IDENTIFICATION METHOD:  sequencing
                    (D) OTHER INFORMATION:  Protein involved in Phage Abortion (x) PUBLICATION INFORMATION:  N/A (xi) SEQUENCE DESCRIPTION: SEQ ID NO:  2:

Met Ser Ser Phe Phe Tyr Lys Glu Ile Leu Arg Met Thr Leu Arg
                5                   10                  15

Phe Phe Thr Val Thr Asp Glu Tyr Ile Ala Tyr Leu Arg Lys Phe Glu
                20                  25                  30

Ser Lys Val His Tyr Gln Tyr Glu Asn Asn Ala Ser Thr Tyr Val Gly
                35                  40                  45

Val Val Leu Lys Lys Asn Asp Phe Asn Tyr Phe Ile Pro Leu Ser Ser
            50                  55                  60

Tyr Lys Lys Gly Asn Pro Glu Lys Asp Lys Ala Met Lys Lys Arg Ser
65                  70                  75

Arg Ile Val Thr Arg Leu Phe Glu Ile Gly Asn Ile Asn Asn Pro Leu
80                  85                  90                  95

Gly Tyr Leu Leu His His Asn Met Ile Pro Val Pro Asp Ser Glu Leu
                100                 105                 110

Ile Pro Leu Pro Leu Asp Leu Lys Lys Pro Lys His Lys Met Met Gln
                115                 120                 125

Lys Gln Leu Ile Tyr Met Lys Ser Ile Ser Glu Lys Ile Glu Asn Lys
                130                 135                 140

Ser Glu Val Val Tyr Arg Lys Ala Ala His Glu Lys Asp Gly Tyr Tyr
                145                 150                 155

Leu Lys Phe Ser Cys Asp Phe Lys Leu Leu Glu Ala Lys Ala Thr Leu
160                 165                 170                 175

Tyr Ser Lys Lys Ser Thr Phe Gln
                180

(2) INFORMATION FOR SEQ ID NO:3:

(i) SEQUENCE CHARACTERISTICS:
                    (A) LENGTH:  11
                    (B) TYPE:  Nucleotide
                    (C) STRANDEDNESS:  Single
                    (D) TOPOLOGY:  Linear (ii) MOLECULE TYPE:
                    (A) DESCRIPTION:  Synthetic RNA (iii) HYPOTHETICAL:  No (iv) ANTI-SENSE:  No (v) FRAGMENT TYPE:  N/A (vi) ORIGINAL SOURCE:
                    (A) ORGANISM:  N/A
                    (B) STRAIN:
                    (C) INDIVIDUAL ISOLATE:  W1
                    (D) DEVELOPMENTAL STAGE:  N/A
                    (E) HAPLOTYPE:  N/A
                    (F) TISSUE TYPE:  N/A
                    (G) CELL TYPE:  N/A
```

-continued

```
            (H) CELL LINE:  N/A
            (I) ORGANELLE:  N/A (vii) IMMEDIATE SOURCE:
            (A) LIBRARY:  N/A
            (B) CLONE:  N/A (viii) POSITION IN GENOME:  N/A (ix) FEATURE:
            (A) NAME/KEY:
            (B) LOCATION:  N/A
            (C) IDENTIFICATION METHOD:  sequencing
            (D) OTHER INFORMATION:  Synthetic RNA (x) PUBLICATION INFORMATION:  N/A (xi) SEQUENCE DESCRIPTION:  SEQ ID NO:  3:

UCUUUCCUCC A                                                            11
```

DNA ENCODING PHAGE RESISTANCE PROTEIN

BACKGROUND OF THE INVENTION (1) Summary of the Invention

The present invention relates to DNA encoding a phage resistance protein. In particular the present invention relates to plasmid pSRQ900 containing DNA which encodes Abi900 containing 183 amino acids. The plasmid when provided in dairy starter cultures imparts phage resistance.

(2) Description of Related Art

For many years, industrial *Lactococcus lactis* strains have been selected for their ability to rapidly produce lactic acid and to develop flavors in dairy fermentations. Bacteriophages able to inactivate these strains have been identified as the main causative agent for fermentation failures (Jarvis et al, Intervirology 32:2–9 (1991)). Lactococcal phages are currently classified in 12 genetically distinct group or species, but only the species 936, c2 and P335 are responsible for most large scale phage attacks worldwide (Moineau et al., J. Dairy Sci. 79:2104–2111 (1996)).

To cope with this diverse phage population, *L. lactis* has developed numerous natural self-defense capabilities and most of them are encoded on plasmids. These natural defense systems are currently classified in four groups based on their mode of action (Garvey et al., Int. Dairy J. 5:905–947 (1995)): blocking of phage adsorption, blocking of phage DNA penetration, restriction/modification system, and abortive infection (Abi). A resistance modification mechanism is described in U.S. Ser. No. 08/424,641. Among the four groups, Abi is believed to be the most powerful (Sing, W. S. et al., J. Dairy Sci. 73:2239–2251 (1990)). Typically, in a lactococcal abortive infection, the phage lytic cycle is terminated intracellularly by the Abi protein and the host is killed. This suicidal outcome limits phage dissemination which can be visualized by the absence of plaque or by a reduction in plaque size. So far, eleven lactococcal Abi have been characterized to the molecular level: AbiA (Hill et al., Appl. Environ. Microbiol. 56:2255–2258 (1990)), AbiB (Cluzel et al., Appl. Environ. Microbiol. 57:3547–3551 (1991)), AbiC (Durmaz et al., J. Bacteriol. 174:7463–7469 (1992)), AbiD (McLandsborough et al., Appl. Environ. Microbiol. 61:2023–2026 (1995)), AbiD1 (Anba et al., J. Bacteriol. 177:3818–3823 (1995)), AbiE (Garvey et al., Appl. Environ. Microbiol. 61:4321–4328 (1995)), AbiF (Garvey et al., Appl. Environ. Microbiol. 61:4321–4328 (1995)), AbiG (O'Connor et al., Appl. Environ. Microbiol. 63:3075–3082 (1996)), AbiH (Prévots et al., FEMS Microbiol. Lett. 142:295–299 (1996)), AbiJ (Deng et al., FEMS Microbiol. Lett. 146:149–154 (1997)) and AbiK (Emond et al., Appl. Environ. Microbiol. 63:1274–1283 (1997)), out of which only AbiD, AbiD1 and AbiF share protein homology. The availability of such a diverse group of Abi proteins most likely reflects differences in their mode of action and is probably responsive of the heterogeneity in lactococcal phage populations.

Many phage-resistant *L. lactis* strains have been constructed by introducing Abi systems into phage-sensitive strains. Extensive use of these strains in commercial applications led to the emergence of phages capable of overcoming these hurdles (Alatossava et al., Appl. Environ. Microbiol. 57:1346–1353 (1991); Moineau et al. Appl. Environ. Microbiol. 59:197–202 (1993)). Another Abi system is described in WO97/20917. Thus, the search for novel and natural antiphage barriers is still a high priority for dairy starter suppliers. These new mechanisms should systematically be tested against members of the 3 common lactococcal phage species to determine their strength and to assess their true potential (Moineau et al., J. Dairy Sci. 79:2104–2111 (1996)).

OBJECTS

It is an object of the present invention to provide DNA encoding a novel abortive infection mechanism (Abi) from *L. lactis* which shares no homology with the previously isolated Abi from *L. lactis*. Further, it is an object of the present invention to provide a novel Abi system which is efficient against 936 and c2 phages. Further still, it is an object of the present invention to provide a method and bacteria which prevent phage inactivation of *Lactococcus lactis* strains. Further still, it is an object of the present invention to provide recombinant bacteria which are very effective in phage inhibition. These and other objects will become increasingly apparent by reference to the following description and the drawings.

BRIEF DESCRIPTION OF DRAWINGS

FIGS. 3A to 3C are a DNA sequence of the 2215-bp EcoRV-BclI fragment from pSRQ900 and deduced amino acid sequence of Abi900. Endonuclease sites used to clone the fragment are indicated. Putative terminators, -35 box, -10 box, and ribosome binding site are underlined. The DNA sequence is also shown in the Appendix in SEQ ID NO:1 along with the deduced amino acids.

DESCRIPTION OF PREFERRED EMBODIMENTS

Figure 1:
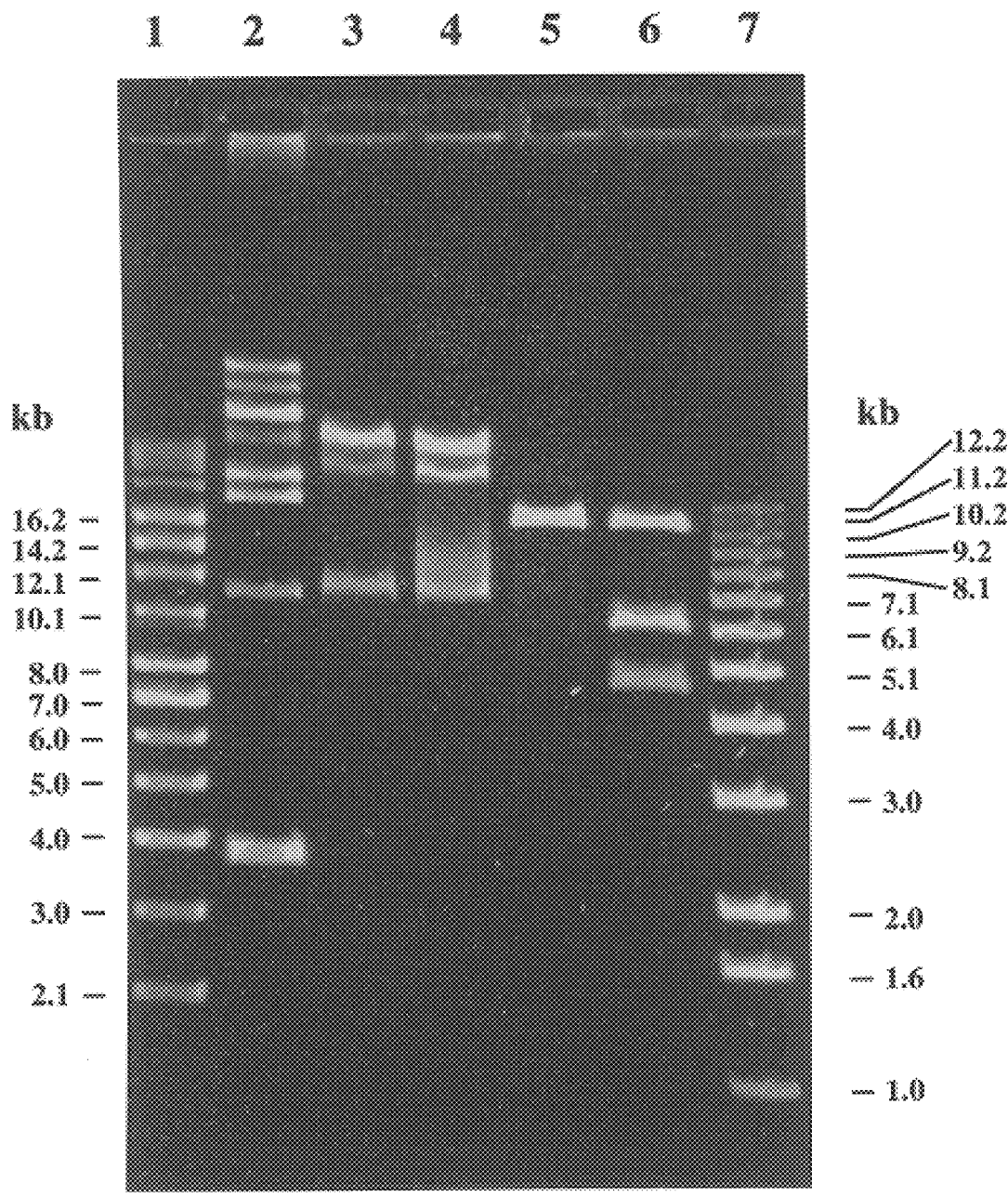
FIG. 1 is an electrophoresis gel identification of the plasmid encoding Ørm in *Lactococcus lactis* subsp. lactis W-37. Lane 1, supercoiled DNA ladder (Gibco/BRL); 2, *L. lactis* W-37; 3, *L. lactis* SMQ16 (pSA3); 4, *L. lactis* SMQ21 (pSA3+pSRQ900); 5, *L. lactis* SMQ16 (pSA3) /EcoRV; 6, *L. lactis* SMQ21 (pSA3+pSRQ900)/EcoRV; 7, 1-kb DNA ladder (Gibco/BRL). Molecular weights on the left correspond to the supercoiled DNA ladder and those on the right correspond to the 1-kb DNA ladder.

The present invention relates to an isolated DNA encoding a protein designated as Abi900 which in a *Lactococcus lactis* increases resistance to phages by aborting infection of the *Lactococcus lactis* by phages.

The present invention also relates to an isolated DNA encoding a protein designated as Abi900 including comprising in plasmid pSRQ900 as contained in *Lactococcus lactis* SMQ-21 deposited as NRRL-B-21681.

Further the present invention relates to an isolated DNA having a nucleotide sequence essentially as set forth in SEQ ID NO:1.

The present invention relates to a recombinant plasmid containing DNA encoding a protein designated as Abi900 which in a *Lactococcus lactis* increases resistance to phages by aborting infection of the *Lactococcus lactis* by the phages. Also the invention relates to a recombinant plasmid containing DNA having a nucleotide sequence as set forth in SEQ ID NO:1 which encodes a protein designated as Abi900.

The present invention relates to a bacterium harboring a recombinant plasmid containing DNA encoding a protein designated as Abi900 which in a *Lactococcus lactis* increases resistance to phage by aborting infection of the *Lactococcus lactis* by the phages. The present invention also relates to a bacterium containing DNA having a nucleotide sequence as set forth in SEQ ID NO:1 which encodes a protein designated as Abi900 which increases phage resistance.

The present invention relates to a method of imparting phage resistance in a bacterium which is sensitive to the phage which comprises transferring DNA encoding a protein designated as Abi900 which increases resistance to phages by aborting infection of *Lactococcus lactis* by the phages into the bacterium to impart the phage resistance. Further the present invention relates to a method for fermenting a dairy product, the improvement which comprises using a culture of *Lactococcus lactis* for the fermenting containing transferred DNA encoding a protein designated as Abi900 which increases resistance to phages by aborting infection of *Lactococcus lactis* by the phages to impart the phage resistance and to produce the dairy product.

The present invention relates to *Lactococcus lactis* naturally lacking in phage resistance and containing transferred DNA encoding a protein designated as Abi900 which increases resistance to phages by aborting infection of *Lactococcus lactis* by the phages, wherein the DNA has a sequence essentially as set forth in SEQ ID NO:1 to impart phage resistance to the *Lactococcus lactis*.

The present invention relates to a protein designated as Abi900 having an amino acid sequence essentially as set forth in SEQ ID NO:1. The present invention further relates to a protein designated as Abi900 having at least 75% identity with the amino acid sequence as set forth in SEQ ID NO:1.

The natural plasmid pSRQ900 was isolated from *Lactococcus lactis* subsp. lactis W37. When introduced into a phage-sensitive *L. lactis* strain, pSRQ900 conferred strong phage resistance against isometric phages of the 936 and prolate phages of the c2 species. The phage resistance mechanism encoded on pSRQ900 is a temperature insensitive abortive infection mechanism (Abi). Plasmid pSRQ900 was mapped and the Abi genetic determinant localized. Cloning and sequencing of the Abi system allowed the identification of a single open reading frame. This ORF coded for a predicted protein of 183 amino acids with an estimated molecular weight of 21.723. No significant DNA or protein homology was observed with databases. This novel phage resistance mechanism was named Abi900. Thus when delivered in an appropriate vector, Abi900 system was efficient against two of the most commonly found lactococcal phage species.

The plasmid pSRQ900 is contained in a deposit of *Lactococcus lactis* SMQ-21 deposited under the Budapest Treaty with the Northern Regional Research Laboratory in Peoria, Ill. on Apr. 21, 1997 as NRRL-B-21681. All restrictions on distribution of the plasmid pSRQ900 will be irrevocably removed upon granting of a patent on this application. DNA plasmid pSRQ700 encoding a restriction or modification system (LlaDCHI) was deposited under the Budapest Treaty as NRRL-B-21337 on Sep. 29, 1994 and is used with pSRQ800 to produce a synergistic result. This DNA is described in U.S. application Ser. No. 08/366,480, filed Dec. 30, 1994, which is incorporated by reference herein and in PCT/NL95/00448. The DNA sequence is deposited with GenBank (V16027). Plasmid pSRQ800 encodes another Abi phage resistant protein which can be used with Abi900. The plasmid PSRQ800 is contained in a deposit of *Lactococcus lactis* SMQ20 deposited under the Budapest Treaty with the Northern Regional Research Laboratory in Peoria, Ill. on May 17, 1995 as NRRL-B-21443.

EXAMPLE

Materials and methods

Bacterial strains, bacteriophages, plasmids and media.

Bacterial strains and bacteriophages used in this study are listed in Table 1.

TABLE 1

Bacterial strains and bacteriophages used in this study

| Bacterial strains and phages | Relevant characteristics[a] Source[b] |
|---|---|
| *Lactococcus lactis* | |
| LM0230 | Plasmid free, host for 936 and c2 phages; Lac⁻McKay et al, 1972 |
| UL8 | Multiple plasmids, host for P335 phages; Lac⁺Moineau et al, 1992 |
| W-37 | Multiple plasmids including pSRQ900; Lac⁺This study |
| SMQ-16 | LM0230 (pSA3); Em$^r$Moineau et al, 1995 |
| SMQ-21 (NRRL B-21681) | LM0230 (pSA3, pSRQ900); Em$^r$ Ørm⁺This study |
| SMQ-42 | LM0230 (pSRQ901); Em$^r$ Ørm⁺This study |
| SMQ-81 | LM0230 (pSRQ904); Em$^r$ Ørm⁺This study |
| SMQ-82 | LM0230 (pSRQ905); Em$^r$ Ørm⁻This study |
| SMQ-86 | UL8 (pSA3); Em$^r$ Emond et al, 1997 |
| SMQ-94 | UL8 (pSA3, pSRQ901); Em$^r$ Ørm⁺This study |
| SMQ-104 | LM0230 (pSRQ909); Em$^r$ Ørm⁻This study |
| SMQ-107 | LM0230 (pSRQ911); Em$^r$ Ørm⁺This study |
| SMQ-123 | LM0230 (pSRQ916); Cm$^r$ Ørm⁺This study |
| SMQ-278 | LM0230 (pSRQ925); Cm$^r$ Ørm⁺This study |
| SMQ-280 | LM0230 (pSRQ926); Em$^r$ Ørm⁻This study |
| *Escherichia coli* DH5α | supE 44 Dlac U169 (f80 lacZDM15) hsdRl7 recA1 Gibco/BRL endA1 gyrA 96 thi-1 relA1 |
| Bacteriophages | |
| øp2 | Small isometric headed, 936 species, 30.5 kbMoineau et al, 1995 |
| øsk1 | Small isometric headed, 936 species, 28.1 kbMoineau et al, 1995 |
| øjj50 | Small isometric headed, 936 species, 30.5 kbMoineau et al, 1995 |
| øc2 | Prolate headed, c2 species, 20.7 kbMoineau et al, 1995 |
| øml3 | Prolate headed, c2 species, 20.2 kbMoineau et al, 1995 |
| øeb1 | Prolate headed, c2 species, 19.6 kbMoineau et al, 1995 |
| øu136 | Small isometric headed, P335 species, 28.8 kbMoineau et al, 1992 |
| øQ30 | Small isometric headed, P335 species, 37.0 kbMoineau et al, 1996 |
| øQ33 | Small isometric headed, P335 species, 29.6 kbMoineau et al, 1996 |

Table 1, Footnotes
[a]Ørm⁺, active phage resistance mechanism; Cm$^r$, chloramphenicol resistance; Em$^r$, erythromycin resistance; Tc$^r$, Tetracycline resistance; Lac, lactose-fermenting ability.

TABLE 2

Plasmids used in this study

| Plasmid | Relevant characteristics | Source |
|---|---|---|
| pBS | Cloning vector for sequencing, Ap$^r$, 2.9-kb | Stratagene |
| pMIG3 | Shuttle vector, Cm$^r$, 5.5-kb | Wells et al, 1993 |
| pSA3 | Shuttle vector, Cm$^r$ Tc$^r$ Em$^r$, 10.2-kb | Dao and Ferretti, 1985 |
| pSRQ900 | Resident plasmid of W37, Ørm$^+$, 11-kb | This study |
| pSRQ901 | 11.0-kb NcoI fragment from pSRQ900 cloned into pSA3; Cm$^s$ Tc$^r$ Em$^r$ | This study |
| pSRQ904 | 4.6-kb EcoRI fragment from pSRQ900 cloned into pSA3; Cm$^s$ Tc$^r$ Em$^r$ | This study |
| pSRQ905 | 5.9-kb EcoRI fragment from pSRQ900 cloned into pSA3; Cm$^s$ Tc$^r$ Em$^r$ | This study |
| pSRQ909 | 4.8-kb EcoRV fragment from pSRQ900 cloned into pSA3; Cm$^s$ Tc$^r$ Em$^r$ | This study |
| pSRQ911 | 6.2-kb EcoRV fragment from pSRQ900 cloned into pSA3; Cm$^r$ Tc$^s$ Em$^r$ | This study |
| pSRQ916 | 4.3-kb HindIII fragment from pSRQ900 cloned into pMIG3; Cm$^r$ | This study |
| pSRQ925 | 2.2-kb EcoRV-BclI fragment from pSRQ900 cloned into pMIG3; Cm$^r$ | This study |
| pSRQ926 | 4.9-kb BglII fragment from pSRQ900 cloned into BamHI site of pSA3; Cm$^r$Tc$^s$ Em$^r$ | This study |

Ørm$^+$, active phage resistance mechanism; Ap$^r$, ampicillin resistance; Cm$^r$, chloramphenicol resistance; Cm$^s$, sensitive to chloramphenicol; Em$^r$, erythromycin resistance; Tc$^r$, tetracycline resistance; Tc$^s$, sensitive to tetracycline.

*Escherichia coli* was grown in LB (Sambrook et al., Molecular cloning: a laboratory manual, 2nd ed. Cold Spring Harbor Laboratory, Cold Spring Harbor, N.Y. (1989)) at 37° C. *Lactococcus lactis* was grown in M17 (Terzaghi and Sandine, Appl. Environ. Microbiol. 29:807–813 (1976)) supplemented with 0.5% glucose (GM17) except for strain W-37 which was grown in M17 supplemented with 0.5% lactose (LM17). When needed, antibiotics were added to media for selection and plasmid maintenance as follows: for *E. coli*, 50 µg/ml ampicillin, 10 µg/ml tetracycline, and 20 µg/ml chloramphenicol; for *L. lactis*, 5 µg/ml chloramphenicol, 5 µg/ml erythromycin.

Bacteriophage propagation and assays.

Phages were propagated by transferring 50 µl of phage stock to 10 ml GM17/10 mM CaCl$_2$ inoculated (1%) with an overnight culture of the host strain. Cultures were incubated at 30° C. until lysis and filtered through 0.45µm filter (Acrodisk, Gelman Sciences, Ann Arbor, Mich.). In order to obtain high phage titer, the newly amplified phages were propagated once more as follows: GM17 was inoculated (1%) with host strain and grown at 30° C. until reaching an O.D.$_{600}$ of 0.1. CaCl$_2$ was then added at a concentration of 10 mM and 50 µl of phage suspension from the first propagation were added. The cultures were incubated at 30° C. until lysis and filtered. Phage titer was determined by the method of Jarvis (Jarvis, A. W., Appl. Environ. Microbiol. 36:785–789 (1978)). Efficiency of plaquing (EOP) and asdorption assays were performed as described by Sanders and Klaenhamer (Sanders, M. E., et al., Appl. Environ. Microbiol. 40:500–506 (1980)). Cell survival was assayed by the method of Behnke and Malke (Behnke, D., et al., Virology 85:118–128 (1978)) using a multiplicity of infection (MOI) of 5.

DNA isolation, manipulation and sequencing.

Plasmid DNA was isolated from *E. coli* as described by Sambrook et al. (Molecular cloning: a laboratory manual, 2nd ed. Cold Spring Habor Laboratory, Cold Spring Harbor, N.Y. (1989)). The method of O'Sullivan and Klaenhammer (O'Sullivan, D. J., et al., Appl. Environ. Microbiol. 59:2730–2733 (1993)) was used for isolation of plasmid DNA from *L. lactis*. Restriction and modification enzymes were used according to the manufacturer's recommendations (Boehringer GmbH, Mannheim, Germany). DNA manipulation was carried out essentially as described by Sambrook et al. (Molecular cloning: a laboratory manual, 2nd ed. Cold Spring Harbor Laboratory, Cold Spring Harbor, N.Y. (1989)). Competent *E. coli* cells were prepared and transformed with the gene pulser II apparatus as described by the manufacturer (BioRad, LaJolla, Calif.). The methods for preparing competent cells and electrotransformation of *L. lactis* have been described elsewhere (Holo and Nes, Appl. Environ. Microbiol. 55:3119–3123 (1989)). DNA to be sequenced was cloned in pBS and nested deletions were generated on each side of inserted DNA using ERASE-A-BASE kit (Promega, Madison, Wis.). Plasmid DNA from the selected mutants was purified with Qiagen plasmid kit (Qiagen, Chatsworth, Calif.) and used in the sequencing reactions with the DyeDeoxy Terminator Taq sequencing kit. Both strands were sequenced by use of T7 and T3 primers. Products were separated on a model 373A automated DNA sequencing system (Applied Biosystems, Foster City, Calif.).

DNA and protein sequence analysis.

The Genetic computer group sequence analysis software package was used to run standard analysis on DNA and putative proteins deduced from the nucleic acid sequence (Devereux et al, Nucleic Acids Res. 12:387–395 (1984)). Searches were performed with GenBank, release 97.0 (10/96); EMBL, release 48.0 (9/96); PIR-Protein, release 50.0 (9/96); SWISS-PROT, release 33.0 (3/96); and PROSITE, release 13.0 (12/95). Program Propsearch (Hobohm and Sander, J. Mol Biol. 251:390–399 (1995)) was used to find putative protein families that failed to show homology with programs based on primary sequence comparisons (BLAST, FASTA). The putative ribosome-binding sites were identified by alignment with the 3'-end of *L. lactis* 16S-rRNA (3'-UCUUUCCUCCA; (Ludwig et al, J. Gen. Microbiol. 131:543–551 (1985)) and the free-energy was calculated by the method of Freier et al. (Freier, S. M., et al., Proc. Natl. Acad. Sci. USA 83:9373–9377 (1986)).

Results

The phage-resistance mechanism (Ørm) in strain W-37 is plasmid-encoded.

*L. lactis* subsp. lactis W-37 is particularly resistant to phage infection (data not shown). This strain carry several plasmids which could potentially encode a Ørm. The cryptic plasmids from W-37 were co-electroporated in the phage-sensitive strain *L. lactis* LM0230 along with the shuttle vector pSA3 (containing an erythromycin resistance gene, Em$^r$) at a DNA mass-ratio of 10:1. A number of colonies growing on GM17+Em plates were tested for phage resistance by spot assay (10$^4$øp2/spot). A few Em$^r$/Ørm$^+$ transformants were obtained and their plasmid content analysed by gel electrophoresis. One Em$^r$/Ørm$^+$ representative was named SMQ-21 (NRRL B-21681). Restriction pattern of EcoRV-digested plasmid DNA from SMQ-21 showed a band of 10.2-kb corresponding to linearized pSA3 and two bands which, when added together, corresponded to a size of about 11-kb (FIG. 1). Those results showed that SMQ-21 carry, in addition to pSA3, a 11-kb plasmid which confers phage resistance. This natural plasmid was named pSRQ900.

The Ørm in pSRQ900 is effective against phages of the 936 and c2 species.

The effectiveness of the Ørm encoded by pSRQ900 was tested against phages belonging to the three main species known to impede industrial fermentations, namely 936, c2 and P335. The Ørm in pSRQ900 led to complete absence of plaques (EOP<10$^{-8}$) when *L. lactis* SMQ-21 was challenged against three strains of the 936 species (Table 3). Similar results were obtained with three strains of the c2 species. pSRQ901, a functional derivative of pSRQ900 carrying a selectable marker, was introduced into a P335-sensitive host (UL8) and challenged against three phages belonging to the P335 species. EOPs were not affected by the presence of the Ørm in that host (Table 3). Those results showed that the Ørm encoded by pSRQ900 confers high resistance against the c2 and 936 species but has no effect on phages of the P335 species.

TABLE 3

EOPs of lactococcal phages at 30° C. on *Lactococcus lactis* strains harboring pSRQ900

| Phage | EOP |
|---|---|
| 936 species[a] | |
| Øp2 | <10$^{-8}$ |
| Øsk1 | <10$^{-8}$ |
| Øjj50 | <10$^{-8}$ |
| c2 species[a] | |
| Øc2 | <10$^{-8}$ |
| Øm13 | <10$^{-8}$ |
| Øeb1 | <10$^{-8}$ |
| P335 species[b] | |
| Øu136 | 1.0 |
| ØQ30 | 1.0 |
| ØQ33 | 1.0 |

[a]The EOP of the 936 and c2 phages was tested on *L. lactis* SMQ-21.
The EOP of these phages is 1.0 on *L. lactis* SMQ-16.
[b]The EOP of the P335 phages was tested on *L. lactis* SMQ-94.
The EOP of these phages is 1.0 on *L. lactis* SMQ-86.

Temperature sensitivity.

The efficiency of the Ørm was assayed against phage p2 at three temperatures regularly used in industrial dairy fermentations. No reduction in EOP (<10$^{-8}$) was observed at 21° C., 30° C. and 38° C., indicating that the Ørm encoded by pSRQ900 is heat stable.

Type of phage resistance.

In order to identify the type of defense mechanism encoded on pSRQ900, a series of microbiological experiements were conducted. Adsorption assays (Table 4) revealed that phages adsorbed at the same level (80% for øp2 and 65% for øc2) on the phage-sensitive cells as on pSRQ900-carrying cells. These results indicate that pSRQ900 does not code for an adsoption blocking mechanism. Cell-free extracts prepared from SMQ-21 were incubated at 30° C. overnight with genomic DNA from øp2 or *Lactococcus lactis* LM0230. DNA was analyzed on agarose gel and no endonucleolytic activity was observed (data not shown). These results ruled out the presence of host-controlled modifications such as R/M systems. Finally in cell survival assays, the presence of pSRQ900 had no impact on the survival of phage-infected *L. lactis* cells indicating that the host still die upon phage infection (Table 4). Based on the current classification of phage defense mechanisms and all the above results, the ørm encoded on pSRQ900 was classified as an abortive infection mechanism and named Abi900.

TABLE 4

Adsorption and cell survival assays

| Strains | Phages | % Adsorption* | % Cell survival** |
|---|---|---|---|
| SMQ-16 | p2 | 80.7 ± 12.7 | 21.3 ± 2.5 |
| SMQ-42 | p2 | 80.4 ± 11.9 | 19.4 ± 5.1 |
| SMQ-16 | c2 | 66.4 ± 8.28 | 12.7 ± 4.2 |
| SMQ-42 | c2 | 65.9 ± 8.45 | 8.3 ± 5.8 |

*n = 4;
**n = 3

The locus for the Ørm maps on a 2.2-kb EcoRV/BclI fragment of pSRQ900.

Figure 2:
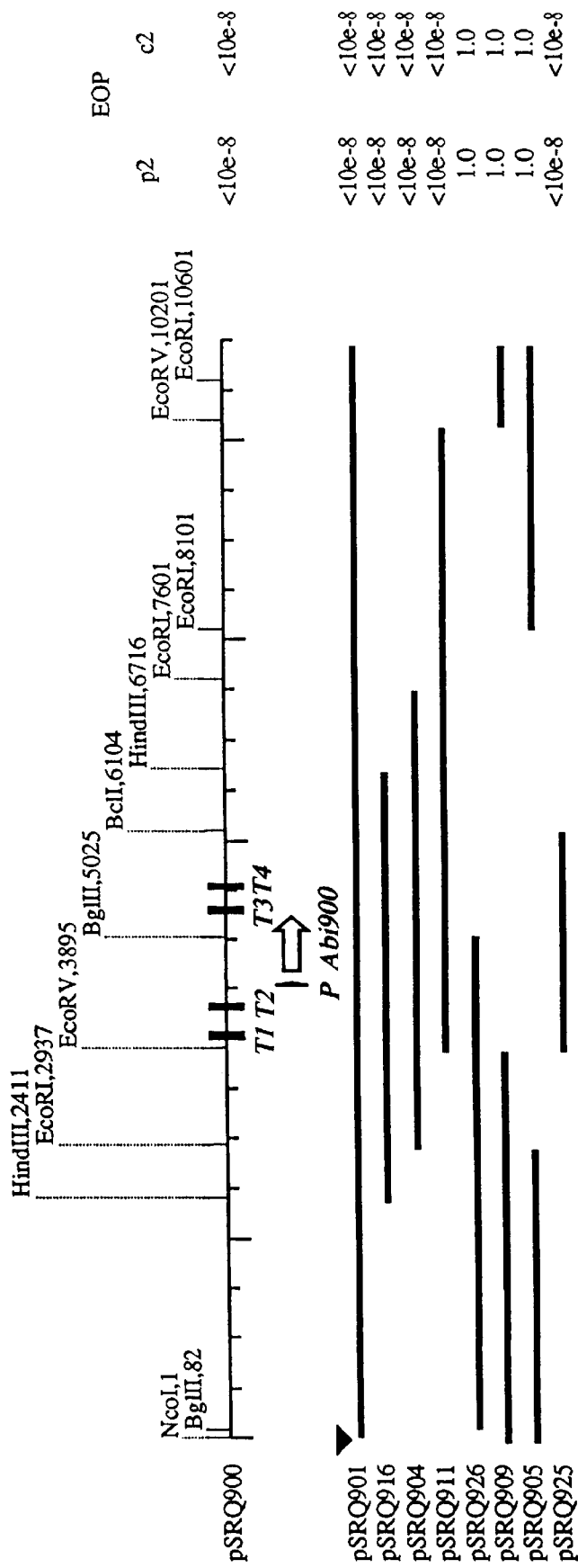
FIG. 2 is a linear restriction map of pSRQ900 and deletion mutants used to localize the genetic determinants of the phage defense mechanism. The following enzymes did not cut pSRQ900: ApaI, AvaI, BalI, BamHI, HpaI, NruI, PstI, PvuI, SalI, ScaI, SmaI, SphI, SstI, XbaI, XhoI. The deletion mutants are represented by horizontal lines below the map and corresponding phenotypes (EOP) on øp2 and øc2 are indicated on the right. Arrowhead above pSRQ901 represent the site (NcoI) which was insertionally inactivated. Putative orf, promoter (P) and terminators (T) shown on the restriction map were inferred from sequence analysis present in FIGS. 3A to 3C.

In order to localize the genetic determinants encoding phage resistance, the restriction map of pSRQ900 and a serie of deletion mutants were generated (FIG. 2). pSRQ900 was cut with EcoRI, EcoRV, HindIII, BclI or NcoI and the fragments were inserted into the shuttle vectors pSA3 or pMIG3. Constructions were introduced into *E. coli*, confirmed by restriction mapping and finally introduced into *L. lactis*. Transformants were tested for their susceptibility to infection by phages of the 936 and c2 species. Results presented in FIG. 2 showed that the DNA sequence between the EcoRV site and the BclI site (pSRQ925) was enough to generate full resistance phenotype (EOP<10$^{-8}$) against øp2 and øc2. Thus, the genetic determinants encoding Ørm against 936 and c2 species clearly maps on the 2.2-kb EcoRV/BclI fragment of pSRQ900.

DNA sequence and analysis of a 2.2-kb EcoRV-BclI fragment from pSRQ900.

This EcoRV-BclI fragment from pSRQ900 which encoded the Ørm was sequenced on both strands. The sequenced fragment contained 2215 nucleotides. The complete sequence was deposited in the GenBank database and is available under the accession number AF001314. The nucleotide 1 to 2215 in the FIGS. 3A to 3C correspond to the nucleotide 3894 to 6108 in the GenBank file.

Only one significant open reading frame (orf) was identified. (FIG. 3A to 3C). This gene was named abi900 and the translated putative protein was named Abi900. abi900 was preceeded by a putative promoter (-35 box [TTGCAT], 20-bp spacer, -10 box [TATAAT] (FIGS. 3A to 3C). The translation start codon was preceeded by a weak ribosome binding site (AAAG; ΔG=-0.1 kcal/mol) located at a proper distance. A tandem repeat (two and a half repeats) located in the promoter region and an inverted repeat encompassing the ribosome binding site were identified. Several terminator-like structures were identified upstream (T1, T2) and downstream (T3, T4) of abi900. It is likely that the transcription product of abi900 would consist of a monocistronic mRNA.

The protein encoded by abi900 is therefore responsible for the Ørm$^+$ phenotype. Abi900 has 183 amino acids and a molecular weight of 21723 Da. The absence of putative signal peptide and integral membrane sequence within the protein suggest that it is located in the cytoplasm. The protein has a high content of positively charged residues (pI=10.5) with seven arginine and 26 lysine residues. Abi900 did not show homology to motifs contained in the Procite database (including helix-turn-helix). It has no known homology to proteins (FASTA) or to proteins deduced from DNA (TFASTA), nor did it showed a similar composition as other proteins (Propsearch). Abi900 is therefore a new protein and a novel Ørm.

We claim:

1. An isolated and purified Abi900 protein having the ability to confer phage-resistance in phage-sensitive *Lactococcus lactis* strains and having the amino acid sequence set forth in SEQ ID NO:2.

2. An isolated and purified Abi900 protein having the ability to confer phage-resistance in phage-sensitive *Lactococcus lactis* strains and comprising the amino acid sequence set forth in SEQ ID NO:2.

3. An isolated and purified nucleic acid molecule encoding Abi900 protein, said protein having the ability to confer phage-resistance in phage-sensitive *Lactococcus lactis* strains and having the amino acid sequence set forth in SEQ ID NO:2.

4. The nucleic acid molecule of claim 3, wherein said nucleic acid molecule is contained within the 2.2 kb EcoRV-BclII restriction fragment of plasmid pSRQ900.

5. The nucleic acid molecule of claim 3, wherein said nucleic acid molecule comprises the nucleic acid sequence set forth in SEQ ID NO:1.

6. A vector comprising a nucleic acid sequence encoding Abi900 protein, said protein having the ability to confer phage-resistance in phage-sensitive *Lactococcus lactis* strains and having the amino acid sequence set forth in SEQ ID NO:2.

7. The vector of claim 6, wherein said nucleic acid sequence is contained within the 2.2 kb EcoRV-BclII restriction fragment of plasmid pSRQ900.

8. The vector of claim 6, wherein said nucleic acid sequence comprises the nucleic acid sequence set forth in SEQ ID NO:1.

9. The vector of claim 6, wherein the vector is designated pSRQ900.

10. A bacterial host cell comprising the vector of any one of claims 6 to 9.

11. The bacterial host cell of claim 10, wherein the host cell is a lactic acid producing bacteria selected from the group consisting of Lactococcus, Lactobacillus, Leuconostocs, Pediococcus, Streptococcus thermophilus, Enterococcus, and Bifidobacterium.

12. The bacterial host cell of claim 10, wherein said host cell is *Lactococcus lactis*.

13. The bacterial host cell of claim 12, wherein the host cell is *Lactococcus lactis* NRRL-B-21681.

14. A method for imparting phage resistance in a bacterium which is sensitive to the phage which comprises transferring DNA encoding Abi900 protein, said protein having the ability to confer phage-resistance in phage-sensitive *Lactococcus lactis* strains and having the amino acid sequence set forth in SEQ ID NO:2.

15. The method of claim 14, wherein the DNA encoding Abi900 protein comprises the nucleic acid sequence set forth in SEQ ID NO:1.

16. The method of claim 14, wherein the bacterium is a *Lactococcus lactis*.

17. The method of claim 16, wherein the bacterium is *Lactococcus lactis* NRRL-B-21681.

18. A method for fermenting a dairy product, said method comprising adding to a dairy product a bacterial host cell comprising a vector comprising a nucleic acid sequence encoding Abi900 protein, said protein having the ability to confer phage-resistance in phage-sensitive *Lactococcus lactis* strains and having the amino acid sequence set forth in SEQ ID NO:2.

19. The method of claim 16, wherein the nucleic acid sequence comprises the nucleic acid sequence set forth in SEQ ID NO:1.

20. The method of claim 16, wherein the vector is designated pSRQ900.

21. The method of claim 16, wherein the bacterium host cell is *Lactococcus lactis* NRRL-B-21681.

* * * * *